United States Patent [19]

Sauer et al.

[11] Patent Number: 4,968,801

[45] Date of Patent: Nov. 6, 1990

[54] PROCESS FOR THE PRODUCTION ERGOLINE DERIVATIVES

[75] Inventors: Gerhard Sauer; Helmut Biere; Gregor Haffer; Andreas Huth, all of Berlin, Fed. Rep. of Germany

[73] Assignee: Schering Aktiengesellschaft, Berlin and Bergkamen, Fed. Rep. of Germany

[21] Appl. No.: 356,620

[22] Filed: May 25, 1989

Related U.S. Application Data

[63] Continuation of Ser. No. 808,764, Dec. 13, 1985, abandoned.

[30] Foreign Application Priority Data

Dec. 13, 1984 [DE] Fed. Rep. of Germany ....... 3445784

[51] Int. Cl.$^5$ ................. C07D 457/02; C07D 457/04; C07D 457/12
[52] U.S. Cl. ...................... 546/67; 546/68; 546/69
[58] Field of Search ............................ 546/67, 68, 69

[56] References Cited

U.S. PATENT DOCUMENTS 3,954,772  5/1976  Bach et al. ........................... 546/67
4,379,790  4/1983  Sauer et al. .......................... 546/69
4,417,051  11/1983 Sauer et al. .......................... 546/69

FOREIGN PATENT DOCUMENTS 204191  7/1959  Fed. Rep. of Germany.

OTHER PUBLICATIONS

Masami Kawase et al., "Journal of the Chemical Society Perkins Transactions I" 1984, 1401 to 1404.

Primary Examiner—Cecilia Shen
Attorney, Agent, or Firm—Millen, White & Zelano

[57] ABSTRACT

Ergoline derivatives of general Formula I

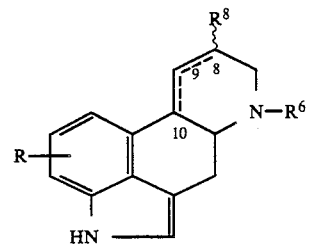

wherein
$C_8$===$C_9$ and $C_9$===$C_{10}$ are both CC-single bonds or one is a C=C-double bond,
$R^6$ is $C_{1-4}$ alkyl,
$R^8$ is methyl, hydroxymethyl, carbonylmethoxy, ureido or N,N-diethylureido, each in the α- or β-position, and
R is hydrogen or nitro, are prepared by dehydrogenation of corresponding 2,3-dihydroergoline derivatives using an electrophilic reagent in an apolar solvent and a base.

14 Claims, No Drawings

PROCESS FOR THE PRODUCTION ERGOLINE DERIVATIVES

This application is a continuation of application Ser. No. 06/808,764, filed Dec. 13, 1985, now abandoned.

BACKGROUND OF THE INVENTION

The invention relates to a process for the production of ergolines.

It is known that the 2,3-double bond can be introduced into 2,3-dihydroergolines using pyrolusite (e.g., U.S. Pat. No. 3,992,385). However, dehydrogenation with pyrolusite has the drawback that the yields are frequently low and cannot be reproduced in larger batches due to fluctuating pyrolusite quality.

Summary of the Invention

It is an object of the present invention, accordingly, to provide a process for the production of ergolines from 2,3-dihydroergolines, in a simpler manner than the prior art which also results in good yields of the desired ergoline.

Upon further study of the specification and appended claims, further objects and advantages of this invention will become apparent to those skilled in the art.

It has now been surprisingly discovered that dehydrogenation using electrophilic reagents in an apolar solvent, in the presence of a base, achieves the objects of this invention in a simple way.

Thus, in one aspect, this invention relates to a process for the production of ergoline derivatives of Formula I

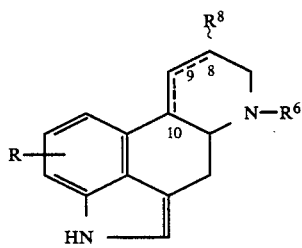

wherein
$C_8 = C_9$ and $C_9 = C_{10}$ are both a CC-single bond or one is a C=C-double bond,
$R^6$ is $C_{1-4}$ alkyl,
$R^8$ is methyl, hydroxymethyl, carbonylmethoxy, ureido, or N,N-diethylureido in the α- or β-position, and
R is hydrogen or nitro, comprising reacting a 2,3-dihydroergoline derivative of Formula II

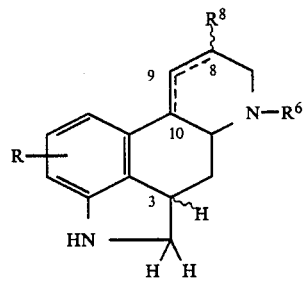

wherein $C_8 = C_9$ and $C_9 = C_{10}$ as well as $R^6$, $R^8$ and R have the above-indicated meanings, and the hydrogen in the 3-position can be in the α- or β-position,
with an electrophilic reagent preferably in an apolar solvent and with a base, at temperatures of −70° to 30° C.

DETAILED DISCUSSION

The compounds of Formula I producible according to this invention either are biologically active per se or can be utilized as intermediate products for the preparation of valuable medicinal agents, as described for e example in EP No. 118848. The compounds of formula I are important drugs from the series of ergot alkaloids such as for example the known lisurid, tergurid or mainly the compounds described in EP No. 118 848. Compounds of formula I are themselves interesting examples of EP-A No. 118 848 or can be converted into these examples by reduction, alkylation or acylation.

They also can be used to prepare each other using conventional reactions, e.g. the nitro-group can be reduced selectively to the amino group with sodium borohydride in the presence of metallic salts, such as nickel-(II) salts or tin(II) salts (A. Nose et al., Chem. Pharm. Bull. 29:1155 [1981] and T. Satoh et al., Chem. Pharm. Bull 29:1443 [1981]).

Suitable $C_{1-4}$ alkyl groups in Formula I include lower alkyl groups, for example, methyl, ethyl, n-propyl, isopropyl, n-butyl, sec-butyl and tert-butyl.

The substituent R can be in positions 12, 13 or 14 of the ergoline molecule.

Non-limiting examples of suitable electrophilic reagents include, for example, halogenating agents, e.g., tert-butyl hypochlorite, N-chlorosuccinimide, N-bromosuccinimide, pyrrolidone hydroperbromide and N-iodosuccinimide, as well as dimethylmethylthiosulfonium tetrafluoroborate, or tosyl chloride, and the like. Electrophiles like alkyl- or acylhalides can not be used.

Non-limiting examples of suitable apolar solvents include, for example, ethers, e.g., tetrahydrofuran, dioxane and dimethoxyethane, chlorinated hydrocarbons, e.g., aliphatic, methylene chloride and chloroform, as well as aromatic hydrocarbons, e.g., benzene and toluene. Polar solvents, e.g., acetonitrile, nitromethane and dimethylformamide, can also be used for performing the process of this invention, but they are not preferred.

Non-limiting examples for suitable bases include alkali metal hydroxides, e.g., sodium and potassium hydroxides, as well as tertiary amines, such as triethylamine and dimethylaniline.

The course of the process of this invention was actually unexpected. It has been known from the work of Kawase (M. Kawase et al., J. Soc. Perkin Trans I:1401 [1984]) that, in the dehydrogenation reaction of indolines to indoles, using the electrophilic agent tert-butyl hypochlorite, acceptable yields are obtained only if, in the first step, N-chlorination is performed in an apolar solvent and then, in a second step, a polar aprotic solvent, such as dimethylformamide, is added to split off hydrogen halide. However, in the process of this invention, halogenation of the indole produced according to the conventional process using indoline, and representing a disturbing feature, does not occur; two separate steps are neither needed nor involved.

The process of this invention is suitably conducted by dissolving the 2,3-dihydroergoline and the base in the preferably apolar solvent, optionally cooling the solution, and gradually adding the electrophilic agent. The reaction is usually terminated after 10–100 minutes using reaction temperatures ranging from −70° to +30° C. Suitably, a protective gas atmosphere is furthermore utilized in the process, e.g., an inert atmosphere, e.g., N₂, Ar, etc. The reaction mixture is subsequently purified by extraction, crystallization and/or chromatography.

Suitable amounts of base are 1.5–10 molar equivalents, and the amounts of electrophilic agent are 1.0–5 molar equivalents, both based on the amount of 2,3-dihydroergoline. The amount of solvent is 10 to 1000 times the amount of starting material, preferably 20 to 100 times.

The starting materials of Formula II are known per se (EP No. 118 848 for example) or can be prepared according to conventional methods.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

EXAMPLE 1

Under argon, 382 mg (1 mmol) of 3-(2,3β-dihydro-6-methyl-13-nitro-8α-ergolinyl)-1,1-diethylurea is dissolved in 30 ml of absolute, freshly distilled tetrahydrofuran in the presence of 0.5 ml of triethylamine and cooled to −40° C. At this temperature, 0.16 ml (1.34 mmol) of tert-butyl hypochlorite, dissolved in 10 ml of absolute, freshly distilled tetrahydrofuran, is added dropwise thereto. After 30 minutes of agitation at −40° C., the batch is stirred into 50 ml of ice and adjusted to be alkaline with 25% strength ammonia solution. Extraction is performed with methylene chloride. The combined organic phases are dried over magnesium sulfate and concentrated. The crude product is chromatographed under pressure on silica gel, with methylene chloride/methanol/diisopropyl ether in a ratio of 80:5:15 (yield 351 mg) and subsequently crystallized from ethyl acetate/diisopropyl ether, thus obtaining 272 mg of 3-(6-methyl-13-nitro-8α-ergolinyl)-1,1-diethylurea (71.7% yield).

$[\alpha]_D = -4.3°$ (0.5% in methanol).

EXAMPLE 2

Analogously to Example 1, the terguride is produced from 3-(2,3β-dihydro-6-methyl-8α-ergolinyl)-1,1-diethylurea as well as 3-(2,3α-dihydro-6-methyl-8α-ergolinyl)-1,1-diethylurea or a mixture of 3α- and 3βH-indolines. Yield: 85%.

$[\alpha]_D = +15°$ (0.5% in chloroform);

3-(9,10-didehydro-6-methyl-14-nitro-8α-ergolinyl)-1,1-diethylurea in 72% yield from 3-(9,10-didehydro-2,3β-dihydro-6-methyl-14-nitro-8α-ergolinyl)-1,1-diethylurea, $[\alpha]_D = +336°$ (0.5% in chloroform);

3-(9,10-didehydro-6-methyl-8α-ergolinyl)-1,1-diethylurea from 3-(9,10-didehydro-2,3β-dihydro-6-methyl-8α-ergolinyl)-1,1-diethylurea. Yield: 45%.

$[\alpha]_D = +312°$ (0.4% in pyridine);

1,1-diethyl-3-(13-nitro-6-n-propyl-8α-ergolinyl)urea from 1,1-diethyl-3-(2,3α-dihydro-13-nitro-6-n-propyl-8α-ergolinyl)urea. Yield: 82%.

$[\alpha]_D = +2°$ (0.5% in chloroform);

1,1-diethyl-3-(6-n-propyl-8α-ergolinyl)urea from 1,1-diethyl-3-(2,3β-dihydro-6-n-propyl-8α-ergolinyl)urea. Yield: 71%.

$[\alpha]_D = +38°$ (0.5% in pyridine);

6-methylergoline-8β-carboxylic acid methyl ester from 2,3β-dihydro-6-methyl-8β-ergolinecarboxylic acid methyl ester. Yield: 70%.

$[\alpha]_D = -100°$ (0.5% in pyridine); and 3-(9,10-didehydro-6-methyl-12-nitro-8α-ergolinyl)-1,1-diethylurea, in a 67% yield, from 3-(9,10-didehydro-2,3β-dihydro-6-methyl-12-nitro-8α-ergolinyl)-1,1-diethylurea;

$[\alpha]_D = -408°$ (0.5% in chloroform).

EXAMPLE 3

Under argon, 34 mg (0.1 mmol) of 3-(2,3β-dihydro-6-methyl-8α-ergolinyl)-1,1-diethylurea is dissolved in 3 ml of absolute, freshly distilled tetrahydrofuran in the presence of 0.05 ml of triethylamine and cooled to −40° C. At this temperature, 60 mg (0.12 mmol) of pyrrolidone hydrotribromide is added. The mixture is then stirred for 20 minutes at −20° C. Then the reaction mixture is stirred into 10 ml of ice and made alkaline with 25% ammonia solution. The organic phase is extracted with methylene chloride. The combined organic phases are dried over magnesium sulfate and concentrated, thus obtaining 1,1-diethyl-3-(6-methyl-8α-ergolinyl)urea in a 60% yield.

$[\alpha]_D = +15°$ (0.5% in chloroform).

EXAMPLE 4

Under argon, 38 mg (0.1 mmol) of 3-(2,3β-dihydro-6-methyl-13-nitro-8α-ergolinyl)-1,1-diethylurea in 2 ml of absolute, freshly distilled tetrahydrofuran is combined with 47 mg (0.24 mmol) of dimethylmethylthiosulfonium fluoroborate, and the mixture is agitated for 20 minutes at room temperature. For working-up purposes, the batch is poured on 10 ml of ice and rendered alkaline with 25% strength ammonia solution. The organic phase is extracted repeatedly with methylene chloride. The extracts are dried over magnesium sulfate and concentrated. The crude product is purified over a preparative silica gel plate with methylene chloride/methanol 9:1 as the eluent, thus obtaining 28 mg of 3-(2,3β-dihydro-6-methyl-1-methylthio-13-nitro-8α-ergolinyl)-1,1-diethylurea.

At room temperature, 25 mg of the previously obtained 3-(2,3β-dihydro-6-methyl-1-methylthio-13-nitro-8α-ergolinyl)-1,1-diethylurea is agitated in 0.5 ml of methanol with 0.5 ml of 7N potassium hydroxide solution under argon. After 2 hours, the batch is combined under ice cooling with saturated sodium chloride solution and extracted with methylene chloride. The organic phases are washed neutral with saturated sodium chloride solution and water, and dried over magnesium sulfate. The organic phases are concentrated. The yield of 3-(6-methyl-13-nitro-8α-ergolinyl)-1,1-diethylurea is quantitative.

[α]$_D$=−4° (0.5% in chloroform).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of an ergoline compound of the formula

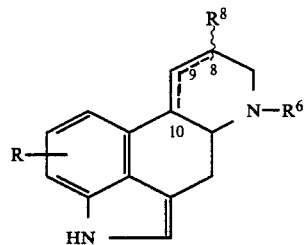

wherein
C$_8$═══C$_9$ and C$_9$═══C$_{10}$ are both CC-single bonds or one is a C—C single bond and the other is a C═C double bond,
R$^6$ is C$_{1-4}$ alkyl,
R$^8$ is methyl, hydroxymethyl, carbonylmethoxy, ureido or N,N-diethylureido, each in the α- or β-position, and
R is hydrogen or nitro, consisting essentially of reacting the corresponding 2,3-dihydroergoline compound of the formula

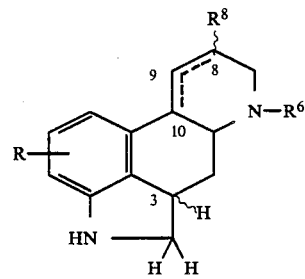

with effective amounts of an electrophilic reagent and a base to directly produce an ergoline compound of the formula I wherein said electrophilic reagent and said base are effective to dehydrogenate said 2,3-dihydroergoline compound whereby an ergoline compound of formula I is directly produced.

2. A process of claim 1, wherein the reaction is conducted in an apolar solvent.

3. A process of claim 1, wherein the reaction is conducted at a temperature of −70° to 30° C. conducted at a temperature of −70° to 30° C.

4. A process of claim 2, wherein the reaction is

5. A process of claim 2, wherein the electrophilic reagent is t-butyl hypochlorite, N-chlorosuccinimide, pyrrolidone hydroperbromide, N-bromosuccinimide, N-iodosuccinimide, or tosyl chloride.

6. A process of claim 2, wherein the apolar solvent is tetrahydrofuran, dioxane, dimethoxyethane, a chlorinated aliphatic hydrocarbon or an aromatic hydrocarbon, wherein said apolar solvent is an effective medium to permit the dehydrogenation of said 2,3-dihydroergoline compound.

7. A process of claim 2, wherein the base is sodium hydroxide, potassium hydroxide, triethylamine or dimethylaniline.

8. A process of claim 5, wherein the apolar solvent is tetrahydrofuran, dioxane, dimethoxyethane, a chlorinated aliphatic hydrocarbon or an aromatic hydrocarbon, wherein said apolar solvent is an effective medium to permit the dehydrogenation of said 2,3-dihydroergoline compound.

9. A process of claim 6, wherein the base is sodium hydroxide, potassium hydroxide, triethylamine or dimethylaniline.

10. A process of claim 2, wherein the electrophilic reagent is tert-butyl hypochlorite and the reaction is conducted in a single step.

11. A process of claim 2, wherein tetrahydrofuran is the apolar solvent.

12. A process of claim 2, wherein triethylamine is the base.

13. A process of claim 2, wherein the electrophilic reagent is tert-butyl hypochlorite and the reaction is conducted in a single step, tetrahydrofuran is the apolar solvent and triethylamine is the base.

14. A process for the production of an ergoline compound of the formula

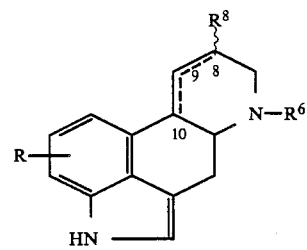

wherein
C$_8$═══C$_9$ and C$_9$═══C$_{10}$ are both C—C single bonds or one is a C—C single bond and the other is a C═C double bond,
R$^6$ is C$_{1-4}$ alkyl,
R$^8$ is methyl, hydroxymethyl, carbonylmethoxy, ureido or N,N-diethylureido, each in the α- or β-position, and
R is hydrogen or nitro,
comprising reacting the corresponding 2,3-dihydroergoline compound of the formula

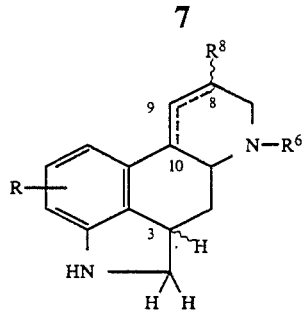

with effective amounts of an electrophilic reagent and a base to directly produce an ergoline compound of the formula I wherein said electrophilic reagent and said base are effective to dehydrogenate said 2,3-dihydroergoline compound whereby an ergoline compound of formula I is directly produced, and wherein said electrophilic reagent is t-butyl hypochlorite, N-chlorosuccinimide, pyrrolidone hydroperbromide, N-bromosuccinimide, N-iodosuccinimide, or tosyl chloride.

* * * * *